US00PP26142P2

(12) United States Plant Patent
Dummen

(10) Patent No.: US PP26,142 P2
(45) Date of Patent: Nov. 24, 2015

(54) ***PELARGONIUM* PLANT NAMED 'DUETEMEZLE'**

(50) Latin Name: *Pelargonium zonale*
Varietal Denomination: Duetemezle

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 35 days.

(21) Appl. No.: 13/987,067

(22) Filed: Jul. 1, 2013

(51) Int. Cl.
*A01H 5/02* (2006.01)

(52) U.S. Cl.
USPC ..... Plt./325

(58) Field of Classification Search
USPC ..... Plt./325
CPC ..... A01H 5/0277
See application file for complete search history.

*Primary Examiner* — Keith O. Robinson
(74) *Attorney, Agent, or Firm* — C. A. Whealy

(57) ABSTRACT

A new and distinct cultivar of Zonal Geranium plant named 'Duetemezle', characterized by its upright plant habit; vigorous growth habit; freely basal branching habit; freely flowering habit; large red purple and dark red-colored semi-double flowers; and good garden performance.

1 Drawing Sheet

Botanical designation: *Pelargonium zonale.*
Cultivar denomination: 'DUETEMEZLE'.

BACKGROUND OF THE INVENTION

The present invention relates to a new and distinct cultivar of Zonal Geranium plant, botanically known as *Pelargonium zonale,* and hereinafter referred to by the name 'Duetemezle'.

The new Zonal Geranium plant is a product of a planned breeding program conducted by the Inventor in Rheinberg, Germany. The objective of the breeding program is to create new vigorous Zonal Geranium plants with numerous attractive flowers.

The new Zonal Geranium plant originated from a cross-pollination made by the Inventor in July, 2005 in Rheinberg, Germany of a proprietary selection of *Pelargonium zonale* identified as code number F-0606-016, not patented, as the female, or seed, parent with a proprietary selection of *Pelargonium zonale* identified as code number F-08-005, not patented, as the male, or pollen, parent. The new Zonal Geranium plant was discovered and selected by the Inventor as a single flowering plant from within the progeny of the stated cross-pollination in a controlled greenhouse environment in Rheinberg, Germany in May, 2010.

Asexual reproduction of the new Zonal Geranium plant by vegetative terminal cuttings in a controlled greenhouse environment in Rheinberg, Germany since June, 2011 has shown that the unique features of this new Zonal Geranium plant are stable and reproduced true to type in successive generations.

SUMMARY OF THE INVENTION

Plants of the new Zonal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duetemezle'.

These characteristics in combination distinguish 'Duetemezle' as a new and distinct Zonal Geranium plant:

1. Upright plant habit.
2. Vigorous growth habit.
3. Freely basal branching habit.
4. Dark green-colored leaves.
5. Freely flowering habit.
6. Large red purple and dark red-colored semi-double flowers.
7. Good garden performance.

Plants of the new Zonal Geranium differ primarily from plants of the female parent selection in branching habit as plants of the new Zonal Geranium are more freely branching than plants of the female parent selection. In addition, plants of the new Zonal Geranium and the female parent selection differ slightly in flower color as plants of the female parent selection have more reddish-colored flowers.

Plants of the new Zonal Geranium differ primarily from plants of the male parent selection in leaf color as plants of the male parent selection have lighter green-colored leaves.

Plants of the new Zonal Geranium can be compared to plants of the *Pelargonium zonale* 'Hot Spot Purple', not patented. In side-by-side comparisons conducted in Rheinberg, Germany, plants of the new Zonal Geranium differed primarily from plants of 'Hot Spot Purple' in the following characteristics:

1. Plants of the new Zonal Geranium were shorter and broader than plants of 'Hot Spot Purple'.
2. Plants of the new Zonal Geranium had smaller leaves than plants of 'Hot Spot Purple'.
3. Plants of the new Zonal Geranium had larger flower umbels than plants of 'Hot Spot Purple'.
4. Plants of the new Zonal Geranium had shorter and thicker peduncles than plants of 'Hot Spot Purple'.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant.

The photograph comprises a side perspective view of a typical flowering plant of 'Duetemezle' grown in a container.

DETAILED BOTANICAL DESCRIPTION

The aforementioned photograph and following observations and measurements describe plants grown during the summer in 12-cm containers in a glass-covered greenhouse in Rheinberg, Germany and under cultural practices typical of commercial *Pelargonium* production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium zonale* 'Duetemezle'.

Parentage:

*Female, or seed, parent.*—Proprietary selection of *Pelargonium zonale* identified as code number F-0606-016, not patented.

*Male or pollen parent.*—Proprietary selection of *Pelargonium zonale* identified as code number F-08-005, not patented.

Propagation:

*Type.*—By vegetative terminal cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; white in color.

*Rooting habit.*—Freely branching; dense.

Plant description:

*Plant and growth habit.*—Upright plant habit; uniformly rounded; densely foliated; vigorous growth habit.

*Branching habit.*—Freely basal branching habit with about five basal branches developing per plant.

*Plant height to top of flower umbels.*—About 19.5 cm.

*Plant height to top of foliar plane.*—About 15 cm.

*Plant width.*—About 34 cm.

*Lateral branches.*—Length: About 11.1 cm. Diameter: About 6.9 mm. Internode length: About 1.5 cm. Texture: Pubescent. Strength: Moderately strong. Color: Close to 144A.

Leaf description:

*Arrangement.*—Alternate; simple.

*Length.*—About 5.1 cm.

*Width.*—About 7.6 cm; depth of leaf sinuses, less than 1 cm.

*Shape.*—Roughly reniform.

*Apex.*—Rounded.

*Base.*—Cordate.

*Margin.*—Crenate.

*Venation pattern.*—Palmate.

*Texture, upper surface.*—Pubescent.

*Texture, lower surface.*—Smooth, glabrous.

*Color.*—Developing and fully expanded leaves, upper surface: Close to 137A; venation, close to 144A. Developing and fully expanded leaves, lower surface: Close to 138A; venation, close to 144A. Zonation pattern: Discernible zonation pattern not observed.

*Petioles.*—Length: About 6.4 cm. Diameter: About 3.6 mm. Texture, upper and lower surfaces: Smooth, glabrous. Color, upper and lower surfaces: Close to 144A.

Flower description:

*Flower arrangement.*—Semi-double type flowers arranged in rounded hemispherical umbels arising from apical leaf axils; umbels displayed above the foliar plane on moderately strong peduncles; flowers face mostly upright to outwardly.

*Fragrance.*—None detected.

*Flowering habit.*—Freely flowering habit, about 22 to 24 flowers per umbel and potentially about five flower umbels developing per plant.

*Flowering season.*—Year-round under greenhouse conditions; in outdoor nurseries and gardens in Germany, flowering is continuous from spring throughout the summer until the autumn; plants begin to flower about eight weeks after planting.

*Flower longevity.*—Individual flowers last about five to seven days on the plant; flowers persistent.

*Umbel height.*—About 7.2 cm.

*Umbel diameter.*—About 10.3 cm.

*Flower diameter.*—About 3.8 cm by 4.3 cm.

*Flower depth* (*height*).—About 1.8 cm.

*Flower buds.*—Length: About 5.7 mm. Diameter: About 4.3 mm. Shape: Ovoid. Color: Close to 144A.

*Petals.*—Quantity per flower: About five arranged in a single whorl. Length: About 3 cm. Width: About 2.2 cm. Shape: Obovate. Apex: Rounded. Base: Attenuate. Margin: Sinuate. Texture, upper and lower surfaces: Smooth, glabrous. Color: When opening, upper surface: Close to 66B and 45B. When opening, lower surface: Close to 74C. Fully opened, upper surface: Close to 66A and 45B; colors becoming closer to 67A and 45A with development. Fully opened, lower surface: Close to 74B; color becoming closer to 74A with development.

*Petaloids.*—Quantity per flower: About three in a single whorl. Length: About 3.7 mm. Width: About 1 mm. Shape: Obovate. Apex: Rounded. Base: Attenuate. Margin: Sinuate. Texture, upper and lower surfaces: Smooth, glabrous. Color: When opening, upper surface: Close to 66C and 45C. When opening, lower surface: Close to 74D. Fully opened, upper surface: Close to 66B and 45C. Fully opened, lower surface: Close to 74C.

*Sepals.*—Quantity per flower: Five arranged in a single whorl. Length: About 1.5 cm. Width: About 3.2 mm. Shape: Ensiform. Apex: Apiculate. Margin: Entire. Texture, upper and lower surfaces: Smooth, glabrous. Color, upper and lower surfaces: Close to 183A and 144A.

*Peduncles* (*umbel stems*).—Length: About 10.1 cm. Diameter: About 4.8 mm. Strength: Moderately strong. Texture: Smooth, glabrous. Color: Close to 144A.

*Pedicels* (*individual flower stems*).—Length: About 2.3 cm. Diameter: About 1 mm. Strength: Moderately strong. Texture: Smooth, glabrous. Color: Close to 64A and 144A.

*Reproductive organs.*—Androecium: Stamen quantity per flower: Five to six. Filament length: About 4.8 mm. Filament color: Close to 155A and 64B. Anther length: About 1 mm. Anther shape: Oblong. Anther color: Close to 26A. Pollen amount: Moderate. Pollen color: Close to 28A. Gynoecium: Pistil quantity per flower: One. Pistil length: About 5 mm. Stigma shape: Crested. Stigma color: Close to 63A. Style length: About 2 mm. Style color: Close to 63B. Ovary color: Close to 191B.

*Seeds and fruits.*—Seed and fruit development have not been observed on plants of the new Zonal Geranium.

Disease & pest resistance: Plants of the new Zonal Geranium have not been observed to be resistant to pathogens and pests common to Zonal Geranium plants.

Garden performance: Plants of the new Zonal Geranium have been observed have good garden performance and to tolerate rain, wind, and temperatures ranging from about 5° C. to about 40° C.

It is claimed:

1. A new and distinct Zonal Geranium plant named 'Duet-emezle' as illustrated and described.

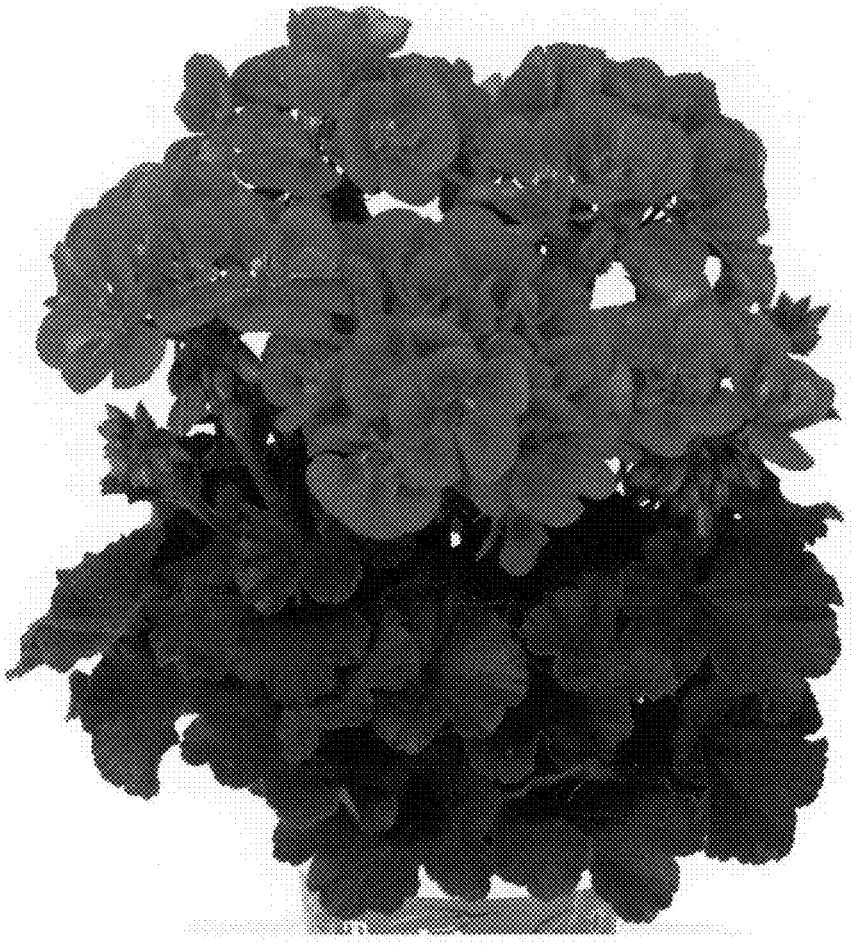

* * * * *